(12) United States Patent
Berner

(10) Patent No.: US 9,724,274 B2
(45) Date of Patent: Aug. 8, 2017

(54) BODY MADE OF CERAMIC MATERIAL

(75) Inventor: Simon Berner, Basel (CH)

(73) Assignee: STRAUMANN HOLDING AG, Basel (CH)

( * ) Notice: Subject to any disclaimer, the term of this patent is extended or adjusted under 35 U.S.C. 154(b) by 710 days.

(21) Appl. No.: 14/124,542

(22) PCT Filed: Jun. 22, 2012

(86) PCT No.: PCT/EP2012/002648
§ 371 (c)(1),
(2), (4) Date: Jan. 24, 2014

(87) PCT Pub. No.: WO2012/175220
PCT Pub. Date: Dec. 27, 2012

(65) Prior Publication Data
US 2014/0178639 A1 Jun. 26, 2014

(30) Foreign Application Priority Data

Jun. 24, 2011 (EP) .................................. 11005158

(51) Int. Cl.
| | | |
|---|---|---|
| A61K 6/02 | (2006.01) | |
| A61L 27/10 | (2006.01) | |
| A61L 27/30 | (2006.01) | |
| A61L 27/42 | (2006.01) | |
| A61L 27/50 | (2006.01) | |
| C04B 41/85 | (2006.01) | |
| C04B 41/00 | (2006.01) | |
| C04B 41/45 | (2006.01) | |
| A61C 8/00 | (2006.01) | |
| C04B 111/00 | (2006.01) | |

(52) U.S. Cl.
CPC .............. *A61K 6/024* (2013.01); *A61L 27/10* (2013.01); *A61L 27/306* (2013.01); *A61L 27/427* (2013.01); *A61L 27/50* (2013.01); *C04B 41/009* (2013.01); *C04B 41/4539* (2013.01); *C04B 41/85* (2013.01); *A61C 8/0012* (2013.01); *A61L 2400/18* (2013.01); *A61L 2430/12* (2013.01); *C04B 2111/00836* (2013.01); *Y10T 428/24355* (2015.01); *Y10T 428/31* (2015.01)

(58) Field of Classification Search
CPC ....... A61K 6/024; A61L 27/10; A61L 27/427; A61L 27/306; A61L 27/50; A61L 2430/12; A61L 2400/18; A61C 8/0012
See application file for complete search history.

(56) References Cited

U.S. PATENT DOCUMENTS

| | | | |
|---|---|---|---|
| 3,919,723 A | 11/1975 | Heimke et al. | |
| 5,368,483 A | 11/1994 | Sutter | |
| 6,165,925 A | 12/2000 | Rieger | |
| 8,029,283 B2 | 10/2011 | Schwarz et al. | |
| 8,568,762 B2 | 10/2013 | Anitua Aldecoa | |
| 2007/0184299 A1* | 8/2007 | Wei ........ | A61L 27/306 428/689 |
| 2008/0098976 A1 | 5/2008 | Harada | |
| 2009/0132048 A1 | 5/2009 | Denzer | |
| 2009/0191280 A1* | 7/2009 | Kokubo ....... | A61L 27/025 424/617 |
| 2009/0191507 A1 | 7/2009 | Charlton | |
| 2010/0068674 A1 | 3/2010 | Zucker | |
| 2010/0136506 A1* | 6/2010 | Park ........... | A61C 13/0003 433/201.1 |
| 2010/0168854 A1 | 7/2010 | Luers | |
| 2012/0164602 A1 | 6/2012 | Lussi et al. | |

FOREIGN PATENT DOCUMENTS

| | | |
|---|---|---|
| EP | 1 777 206 A1 | 4/2007 |
| EP | 1982670 B1 | 4/2007 |
| EP | 1847278 A1 | 10/2007 |
| EP | 1 982 671 A1 | 10/2008 |
| EP | 2 014 319 A1 | 1/2009 |
| EP | 2 191 850 A1 | 6/2010 |
| ES | 2352635 A1 | 2/2011 |
| JP | H08-182755 A | 7/1996 |
| JP | 2004075532 A1 | 3/2004 |
| WO | 2007/046693 A1 | 4/2007 |
| WO | WO2008098976 A2 | 8/2008 |
| WO | 2010/057949 A2 | 5/2010 |
| WO | 2010/094968 A2 | 8/2010 |

OTHER PUBLICATIONS

Translation of Jun. 1, 2016 Office Action issued in Japanese Application No. 2014-516228.
International Search Report mailed Sep. 14, 2012 in PCT/EP2012/002648.
Molenberg, A et al., "Improved osseointegration of a novel, hydrophilic Ti surface—a review", Jan. 1, 2009, vol. 40, No. 1-2, Jan. 1, 2009, pp. 31-35.
Rupp F. et al., "Enhancing surface free energy and hydrophilicity through chemical modification of microstructured titanium implant surfaces", Journal of Biomedical Materials Research Part A, Wiley Periodicals Inc., Hoboken, NY, US, vol. 76A, No. 2, Feb. 1, 2006.
International Search Report mailed Sep. 14, 2012 in PCT/EP2012/002646.
International Preliminary Report on Patentability mailed Dec. 24, 2013 in PCT/EP2012/002648.

* cited by examiner

*Primary Examiner* — Laura Auer
(74) *Attorney, Agent, or Firm* — Oliff PLC

(57) ABSTRACT

Body made of a ceramic material, the body having as an integral part thereof a surface region reaching from the surface of the body down to a predetermined depth. According to the invention, the surface region is enriched with a magnesium component thereby forming a hydrophilic surface area.

18 Claims, No Drawings

BODY MADE OF CERAMIC MATERIAL

FIELD OF THE INVENTION

The present invention relates to a body made of a ceramic material, to a method for improving the hydrophilicity of a body made of a ceramic material, and to the use of the ceramic body as an implant or as an abutment for such an implant, in particular as a dental implant or a dental implant abutment.

BACKGROUND

Implants, such as dental implants, are well known in the art, e.g., U.S. Pat. No. 5,368,483 (Sutter), U.S. Pat. No. 8,029,283 (Schwarz) and US 2010/0068674 (Zucker) incorporated by reference herein.

Dental implants generally comprise an anchoring part, which is designed to be anchored in the jaw bone, and a mounting part, which serves as a base for the direct or indirect attachment of a suprastructure, such as a crown or bridge.

There are one-part dental implant systems, in which the anchoring part and the mounting part are integrally formed of one piece, and two-part dental implant systems, comprising a separate piece, the so-called "abutment", serving as a mounting part.

An abutment is thus a separate mounting part for a dental implant, intended for connecting the part that is anchored in the bone to the suprastructure.

Dental implants generally consist of a material, which is biocompatible and which additionally has favourable mechanical properties.

With regard to the anchoring part, it is required that the dental implant provides good osteointegration.

The term "osteointegration" designates the direct structural and functional connection between living bone and the surface of the load-bearing implant. A good osteointegration means that the implant, after reaching a primary stability by screwing it into the bone, safely ossifies within a short healing time so that a permanent bond between implant and bone is obtained.

Suitable materials for an implant are in general made of a metal, e.g. titanium, or a ceramic, e.g. a zirconium based ceramic.

In contrast to titanium implants, which are dark and therefore mismatch with the colour of natural teeth, ceramic materials have the advantage that their colour can be closely matched to the colour of natural teeth. Efforts have thus been made to provide dental implants, of which at least the parts that are visible after insertion are made of a ceramic material.

Despite these favourable properties, the use of ceramic materials for dental implants is quite often limited by their fatigue stability, which is generally rather low.

A ceramic material with sufficient mechanical stability is disclosed in U.S. Pat. No. 6,165,925. This material is, however, per se not osteointegrative.

Osteointegration has been turned out to be particularly efficient if mechanical roughening of the implant's surface is combined with subsequent etching of the roughened surface. In this regard, EP-A-1 982 670 discloses a process wherein at least a part of the surface is etched with a solution comprising hydrofluoric acid.

However, a further improvement of the osteointegrative properties of the implant is still the subject of on-going research, since it allows a permanent bond between implant and bone to be established in a relatively fast manner, ultimately allowing a shortening of the healing time after the implantation.

SUMMARY OF THE INVENTION

The object of the present invention is thus to provide a ceramic body having improved hydrophilicity.

The present invention thus relates to a body made of ceramic material, the body comprising as an integral part thereof a surface region reaching from the surface down to a predetermined depth. According to the invention, said surface region is enriched with a magnesium component thereby forming a hydrophilic surface area.

Given the fact that the surface region reaches down to a predetermined depth, the body further comprises as a "remainder"—a core region, which is enclosed by said surface region. Since the surface region is an integral part of the body, the surface region and the core region are formed integrally.

In general, the term "enriched" as used in the context of the present invention relates to the surface region of the ceramic body comprising a higher proportion of the magnesium component than the remainder, i.e. the core region, of the body. The term "proportion" as used in this context relates to the molar percentage of magnesium in any form, (in particular ionic form), relative to the total number of atoms or molecules, respectively, of the ceramic material.

As will be shown below, the enrichment in the magnesium component is in general achieved by incorporation of the magnesium component into the ceramic body due to diffusion or permeation. According to a preferred embodiment, the magnesium component is thus integrated in the ceramic material of the surface region. As will be discussed below, the magnesium component is preferably magnesium ions or magnesium oxide (MgO).

Specifically, the body according to the present invention is used as an implant, more specifically as a dental implant.

It has surprisingly been found that the ceramic body of the present invention allows an implant or abutment to be obtained with an improved hydrophilicity. It has also been found that the hydrophilicity achieved according to the present invention is stable; particularly, the hydrophilicity is maintained during storage of the body in aqueous solution.

It has further been found that this improvement of the hydrophilicity goes along with improved osteointegrative properties of the ceramic surface. This renders the body of the present invention particularly suitable for the use as a dental implant or abutment.

The improved hydrophilicity is not only beneficial on the implant's anchoring part, but also on its mounting part, in particular an abutment, or a respective intermediate part, in view of an improved interaction between the implant or abutment and the surrounding soft tissue.

Specifically, the term "hydrophilic" or "hydrophilicity" as used in the context of the present invention refers to a contact angle of the hydrophilic surface area being less than 90°, more preferably less than 30°, most preferably less than 10°.

Without wanting to be bound by the theory, hydrophilicity of the surface playing a crucial role in the osteointegration and/or soft-tissue regeneration process can partly be explained by the fact that it goes along with an improved attachment of certain proteins (e.g. fibrinogen, plasma fibronectin) and the resulting stabilization of the blood clot. This finally results in the faster formation of new bone.

Aiming at a fast healing process, which includes preventing acute or chronic inflammatory processes, the present invention thus allows a quick and mechanically stable osteointegration due to an intimate contact of the implant with the surrounding bone tissue structure.

According to a preferred embodiment of the present invention, the ceramic material of the body of the present invention comprises zirconia. Zirconia ceramic shows no interactions with other dental materials and is electrically neutral. Because of a friendly gum reaction and due to findings that dental plaque seems to be less attached to this material, it bears a very low risk of inflammation. In addition, the material has a light colour and can thus be closely adapted to natural tooth colour.

According to a most preferred embodiment the implant according to the present invention is made of ceramic comprising an yttria-stabilized zirconia. In general, the yttria-stabilized zirconia used is tetragonal in phase. Yttria-stabilized tetragonal zirconia has a very high strength, a high toughness and a good wear resistance.

Apart from yttria-stabilized zirconia, also e.g. alumina-stabilized zirconia or ceria-stabilized zirconia can be used for the present invention. Other ceramic materials, such as zirconia-stabilized alumina, are thinkable. In this regard, the term "ceramic material" is to be understood to also include glass ceramic materials.

In view of achieving a high hydrophilicity without interfering with the intrinsic properties of the material, it is preferred that the surface region reaches from the surface of the body down to a depth of about 10 µm at most, more preferably of about 1 µm at most, more preferably of about 500 nm at most and even more preferably of about 200 nm at most. Within this range, the surface region is thought to be sufficiently thin in order to preserve intrinsic properties of the ceramic material and its surface topography while improving hydrophilicity. Thus, apart from an improved hydrophilicity, the other properties of the ceramic material—e.g. the visual appearance of the body—can be kept essentially unchanged. Also the mechanical properties of ceramics, thus the strength, toughness and wear resistance of e.g. yttria-stabilized tetragonal zirconia can be maintained.

According to a further preferred embodiment of the invention, the proportion of the magnesium component typically increases continuously from the predetermined depth towards the surface of the body. In other words, there is in the surface region, thus, a gradient of the magnesium component decreasing from the surface towards the core region. This is a consequence of the straightforward method of the present invention which will be disclosed in detail below. As a result, the proportion of the magnesium component is highest where it is a major importance for providing hydrophilicity.

According to a further preferred embodiment of the invention, the hydrophilic surface area is formed at least on the portion of the body which is intended to be in contact with bone tissue, since in this portion the improved hydrophilicity is of particular importance.

Alternatively or additionally, it is also thinkable that the hydrophilic surface area is formed at least on the portion of the body that is intended to be in contact with the soft tissue, as it has been found that also the attachment of soft tissue to the implant can be improved by a higher hydrophilicity, although the underlying mechanisms are assumed to be different than the mechanisms leading to improved osteointegration.

According to a specifically preferred embodiment, the hydrophilic surface area is formed on the entire surface of the body. As mentioned above, it is also thinkable that the hydrophilic surface area is formed only on a part of the body.

It is further preferred that at least a part of the hydrophilic surface area has a surface roughness, i.e. a roughened surface, in particular a combination of microscopic and macroscopic roughness, as obtainable by the process as described by EP-A-1982671 (same as U.S. Pat. No. 8,408,906) according to EP-A-1982670. A detailed description for providing microscopic roughness is found in EP-A-1982670 (same as US 2008/0261178 published 23 Oct. 2008), in particular paragraphs [0024] to [0030], [0060] to [0064] and [0079] to [0081], the disclosure of which is hereby incorporated by reference.

The described combination of microscopic and macroscopic surface roughness further contributes to high osteointegrative properties of the implant. In addition to the body described above, the present invention further relates to a method for improving the hydrophilicity of a body. The method comprises the subsequent steps of a) applying at least one magnesium compound selected from the group consisting of a magnesium salt, magnesium oxide, magnesium hydroxide, metallic magnesium and a magnesium containing gel onto the surface of a basic ceramic body;

b) thermally treating the basic ceramic body with the magnesium compound applied thereon at a temperature higher than 200° C., whereby a magnesium component based on the magnesium compound diffuses into the ceramic material. Thereby, a stable bond of the magnesium component and the ceramic body is formed in a sense that rinsing with aqueous solution does not remove the magnesium component.

The temperature of heat treatment b) is preferably set above the decomposition temperature of the magnesium compound. Typically, the temperature of heat treatment b) is lying in the range of about 250° C. to about 1650° C., preferably about 600° C. to about 900° C.

It is understood that the temperature is also dependent on the respective ceramic material of the basic body. For example, for a material of the type Tosoh or MZ111, which are known to a skilled person, as well as for a pre-sintered basic body, the temperature of the thermal treatment b) might be different. The temperature of the thermal treatment preferably ranges from about 250° C. to about 1650° C., more preferably from about 600° C. to about 1500° C., and most preferably from about 800° C. to about 1350° C.

In the context of the present invention the term "magnesium compound" is used for the magnesium species applied onto the ceramic body, whereas the term "magnesium component" is used for the magnesium species that diffuses into the ceramic body and is thereby integrated in the surface region of the body.

Since magnesium ions or MgO is the preferred component to diffuse into the ceramic body, the magnesium compound to be applied onto the surface of the basic ceramic body is preferably a compound which in the course of the thermal treatment forms MgO. Further, magnesium ions are likewise preferred to diffuse into the ceramic body. According to a particularly preferred embodiment, a magnesium salt selected from the group of MgO, $MgCO_3$, $Mg(NO_3)_2$ and $MgSO_4$ is used. Further magnesium compounds suitable for the present invention include e.g. magnesium citrate and magnesium acetate.

The use of $MgCO_3$ is particularly preferred, since allows magnesium to diffuse into the ceramic body, without affecting the surface topography. In view of its use for a dental implant, the osteointegrative properties provided by roughening of the surface can thus be maintained.

As a further preferred magnesium compound, $MgCl_2$ has been shown to result in a particularly high hydrophilicity.

The application of the magnesium compound, such as $MgO$, $MgCO_3$, $Mg(NO_3)_2$, $MgSO_4$ or $MgCl_2$ can be carried out by e.g. soaking/immersion, dipping or drop casting, by embedding into powder, by the use of spin coating, electrophoresis, sandblasting, or by plasma immersion ion implantation (PIII).

Alternatively to the method described above, other methods for the application of the magnesium compound include the application of a magnesium containing gel, physical vapour deposition (PVD), chemical vapour deposition (CVD) and atomic layer deposition (ALD). PVD is thereby particularly preferred whereby preferably MgO is sputtered directly onto the surface. Alternatively, the MgO can be formed on the surface by sputtering magnesium in combination with an oxygen background pressure.

Given the fact that the magnesium component diffuses into the ceramic material, there is no discrete coating and thus no discrete boundary between the magnesium component and the basic body. Consequently, there is no splitting or washing off of the magnesium component, as it is typically seen when a separate coating of an additional material is applied on a ceramic body.

The method of the present invention allows thus a magnesium component to be integrated into the body in a very simple manner. The magnesium component being integrated into the material of the body is in clean contrast to the teaching of EP-A-1847278, relating to titanium and thus to a material for which a diffusion of a magnesium component by the thermal treatment according to step b) would not be obtained.

The actual temperature to achieve a sufficient diffusion of the magnesium component into the ceramic material depends on the specific ceramic material and the magnesium compound used. As mentioned, MgO and/or Mg ions are the preferred components to diffuse and integrate into the ceramic body.

The depth of diffusion of the magnesium component can be adjusted by appropriately setting the temperature and the duration of the thermal treatment according to step b). A skilled person who has become aware of the teaching of the present invention knows how to set these parameters in order to achieve the desired depth of diffusion.

In general, the body of the present invention is prepared using a sintering process. It is in this regard thinkable that method step a), i.e. the application of the magnesium compound, is performed on the (pre-sintered) white body, which is afterwards subjected to the final sintering temperature and thus simultaneously also to the thermal treatment according to step b).

According to a further preferred embodiment of the invention, the thermal treatment is followed by cleaning the dental implant of non-specifically bonded, residual magnesium compound. This cleaning step is preferably performed by rinsing the dental implant with pure water or an aqueous solution like e.g. NaCl solution, or other liquids. In particular if the magnesium compound applied is in solid form other cleaning methods, such as air streaming, brushing and/or polishing can be performed for the removal.

The performance of the washing step can be improved by using ultrasound. Thereby, grains, grain agglomerates or reaction products which loosely adhere to the surface are effectively removed. Alternatively, acid washing is possible.

The dental implant which has been thermally treated and subjected to the above described cleaning step has a hydrophilic surface and is biologically active.

According to a further preferred embodiment of the present invention, the process comprises the step of roughening at least a part of the surface of the basic body by a subtractive treatment before applying the magnesium compound. It is in this context further preferred that the subtractive treatment comprises two sequential roughening steps: a first step for providing a macroscopic surface roughness, e.g. by a sand-blasting, prior to a second step that provides a microscopic surface roughness, e.g. acid etching. In this regard it is referred to the process according to EP-A-1982670 paragraphs [0055] to [0064] (same as US2008/0261178 published 23 Oct. 2008), the disclosure of which is incorporated herein by reference.

In particular, the step of roughening can be performed after the final sintering step, which is carried out after application of the calcium compound on the pre-sintered white body.

As mentioned above, the object achieved by the present invention is particularly useful in the field of implantology, in particular in oral implantology. The present invention thus further relates to the use of the body as an implant, in particular a dental implant.

DETAILED DESCRIPTION

The present invention likewise relates to the use of the body as an abutment for such an implant. All features and advantages mentioned above for an implant, in particular a dental implant, likewise apply to an abutment.

The present invention is further illustrated by way of the following example:

EXAMPLE

Preparation of Samples

Discs of yttria-stabilized zirconia (MZ111 HIP of CeramTec AG) having a machined surface, a thickness of about 1 mm and a diameter of about 5 mm were used.

The discs were cleaned with Deconex 15 PF for 5 minutes using ultra-sound and subjected to a plasma treatment Specifically, the plasma treatment was performed using an apparatus of the type "Femto" (Diener Electronics GmbH+ Co. KG, Ebhausen) using the following parameters: power 35 W, 6 sccm oxygen gas flow (sccm: standard cubic centimeter per minute; 1 sccm=1 cm3 per minute at normal pressure, i.e. 1013 mbar), pressure≈0.1 mbar, time 2.5 minutes).

A $MgCO_3$ slurry prepared by mixing $MgCO_3$ with water in a weight ratio of 1:1 was applied to the discs in a thickness of about 1 to 2 mm.

The discs with the slurry applied thereon were heated to 1150° C. for 2 hours and then cooled in air. The cooled samples were then rinsed using pure water and dried under a stream of argon.

The chemical composition of the surface and the surface region of the discs were determined using X-ray Photoelectron Spectroscopy (XPS). XPS analysis included determination of the normalised atomic percentage as a function of the depth of the material. To this end, the surface material of the sample was subtracted using an argon sputter gun and XPS spectra were taken at different depths. During sputtering, the samples were rotated in order to allow a homogenous subtraction of the material.

Contact Angles (CA)

For three samples, the contact angles were determined using pure water according to the sessile drop method (Easy)prop DSA20 E, Krüss GmbH). A drop size of 0.3 μl was chosen. The contact angles were calculated by fitting a circular segment function to the contour of the droplet placed on the surface ("circle fitting method").

The results of the contact angles as a function of the exposure time to laboratory air are represented below:

| Storage time [days] | CA [°] of Sample 1.1 | CA [°] of Sample 1.2 | CA [°] of Sample 1.3 | Mean CA [°] | Standard Deviation CA [°] |
|---|---|---|---|---|---|
| 0 | 0.0 | 0.0 | 0.0 | 0.0 | 0.0 |
| 2 | 35.0 | 25.8 | 20.5 | 27.1 | 7.3 |
| 5 | 47.4 | 41.9 | 39 | 42.8 | 4.3 |
| 7 | 49.5 | 43.8 | 41.9 | 45.1 | 4.0 |

Chemical Composition

The chemical composition of the disc (i.e. the atomic percentage of the respective elements at a given depth from the surface) as determined by XPS is represented below:

| Depth/[nm] | Zr [%] | Y [%] | C [%] | O [%] | Al [%] | Mg [%] |
|---|---|---|---|---|---|---|
| 0 | 22.8 | 1.9 | 11.8 | 54.7 | 6.1 | 2.7 |
| 50 | 38.8 | 3.0 | 0.0 | 54.8 | 1.8 | 1.7 |
| 100 | 40.9 | 3.0 | 0.0 | 55.1 | 0.8 | 0.3 |
| 200 | 42.0 | 3.0 | 1.0 | 53.8 | 0.0 | 0.2 |
| 350 | 42.4 | 3.1 | 0.0 | 53.3 | 1.0 | 0.2 |
| 500 | 43.0 | 3.1 | 0.0 | 53.7 | 0.0 | 0.2 |

The invention claimed is:

1. An implant system in contact with a bone, the implant system comprising a body made of a ceramic material, wherein
   the body comprises as an integral part thereof a surface region reaching from a surface of the body down to a predetermined depth;
   the surface region is enriched with a magnesium component thereby forming a hydrophilic surface area; and
   the hydrophilic surface area is formed at least on the portion of the body in direct contact with the bone.

2. The implant system according to claim 1, wherein the magnesium component is integrated in the ceramic material of the surface region.

3. The implant system according to claim 1, wherein the magnesium component is magnesium ions or magnesium oxide.

4. The implant system according to claim 1, wherein the surface region reaches down to a depth of 10 μm at most.

5. The implant system according to claim 1, wherein the proportion of the magnesium component increases continuously from the predetermined depth towards the surface of the body.

6. The implant system according to claim 1, wherein the hydrophilic surface area is defined by a contact angle of less than 90°.

7. The implant system according to claim 1, wherein the body is a dental implant.

8. The implant system according to claim 1, wherein the hydrophilic surface area is formed on an entire surface of the body.

9. The implant system according to claim 1, wherein the ceramic material comprises zirconia.

10. The implant system according to claim 9, wherein the ceramic material comprises yttria-stabilized zirconia.

11. The implant system according to claim 1, wherein at least a part of the hydrophilic surface area has a surface roughness obtainable by a surface roughness treatment.

12. An implant system in contact with a soft tissue, the implant system comprising a body made of ceramic material, wherein
   the body comprises as an integral part thereof a surface region reaching from a surface of the body down to a predetermined depth;
   the surface region is enriched with a magnesium component thereby forming a hydrophilic surface area; and
   the hydrophilic surface area is formed at least on the portion of the body in direct contact with the soft tissue.

13. The implant system according to claim 12, wherein the magnesium component is integrated in the ceramic material of the surface region.

14. The implant system according to claim 12, wherein the surface region reaches down to a depth of 10 μm at most.

15. A method for producing the implant system according to claim 1, said method comprising
   a) applying at least one magnesium compound selected from the group consisting of a magnesium salt, magnesium oxide, magnesium hydroxide, metallic magnesium and a magnesium containing gel onto the surface of a basic ceramic body, and
   b) thermally treating the basic ceramic body with the magnesium compound applied thereon at a temperature higher than 200° C., whereby a magnesium component based on the magnesium compound diffuses into the ceramic material.

16. The method according to claim 15, wherein the magnesium compound of step a) is selected from the group consisting of $MgCO_3$, $Mg(NO_3)_2$, $MgCl_2$, $MgSO_4$, Mg-acetate, and combinations thereof.

17. The method according to claim 15, wherein after step b) residual magnesium compound is removed from the surface of the body by rinsing with a liquid, air streaming, brushing acid washing or polishing.

18. The method according to claim 17, wherein the liquid used for rinsing is pure water or an aqueous solution.

* * * * *